US011141068B2

United States Patent
Irisawa

(10) Patent No.: US 11,141,068 B2
(45) Date of Patent: Oct. 12, 2021

(54) REPLACEMENT METHOD FOR A DAMAGED PART OF A LIGHT EMITTER OF A PROBE

(71) Applicant: FUJIFILM Corporation, Tokyo (JP)

(72) Inventor: Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 305 days.

(21) Appl. No.: 16/290,578

(22) Filed: Mar. 1, 2019

(65) Prior Publication Data

US 2019/0192007 A1    Jun. 27, 2019

Related U.S. Application Data

(60) Division of application No. 14/809,755, filed on Jul. 27, 2015, now abandoned, which is a continuation of
(Continued)

(30) Foreign Application Priority Data

Mar. 26, 2013   (JP) ................................ 2013-063581
Mar. 13, 2014   (JP) ................................ 2014-050315

(51) Int. Cl.
*A61B 5/00*     (2006.01)
*G01H 9/00*     (2006.01)
(Continued)

(52) U.S. Cl.
CPC ........... *A61B 5/0095* (2013.01); *G01H 9/004* (2013.01); *G01N 29/22* (2013.01); *G01N 29/24* (2013.01);
(Continued)

(58) Field of Classification Search
CPC ........ A61B 5/0095; A61B 1/07; G01N 29/24; G01N 29/22; G01N 29/2462;
(Continued)

(56) References Cited

U.S. PATENT DOCUMENTS 5,133,032 A      7/1992   Salter et al.
6,057,961 A *    5/2000   Allen ................... G02B 5/3083
                                               359/489.12
(Continued)

FOREIGN PATENT DOCUMENTS

JP          63-127748 A      5/1988
JP        2012-179350 A      9/2012
(Continued)

OTHER PUBLICATIONS

International Search Report issued in PCT/JP2014/057256, dated Apr. 15, 2014.
(Continued)

*Primary Examiner* — Sean D Mattson
(74) *Attorney, Agent, or Firm* — Birch, Stewart, Kolasch & Birch, LLP

(57) ABSTRACT

A photoacoustic probe which prevents foreign substances from entering and of which a portion of a light emitting unit to be easily damaged can be replaced is provided. An acoustic wave detector 24 detects acoustic waves. First and second light guide members 21 and 23, which form the light emitting unit, are arranged in series in a traveling direction of light. A frame body 11 holds the first light guide members 21, the second light guide members 23, and the acoustic wave detector 24. The first light guide members 21, is positioned close to a subject, is undetachably fixed to the frame body 11. Meanwhile, the second light guide members 23, which is positioned close to a light source, is detachably fixed to the frame body 11.

10 Claims, 17 Drawing Sheets

Related U.S. Application Data application No. PCT/JP2014/057256, filed on Mar. 18, 2014.

(51) Int. Cl.
*G01N 29/24* (2006.01)
*G01N 29/22* (2006.01)

(52) U.S. Cl.
CPC ..... *G01N 29/2418* (2013.01); *G01N 29/2462* (2013.01)

(58) Field of Classification Search
CPC ........... G01N 29/2418; G01N 21/1702; G01N 2201/0826; G01N 2201/067; G02B 6/3624; G02B 6/4292
See application file for complete search history.

(56) References Cited

U.S. PATENT DOCUMENTS

| | | | |
|---|---|---|---|
| 2001/0004410 A1* | 6/2001 | Kondo | G02F 1/2255 385/2 |
| 2003/0181802 A1 | 9/2003 | Ogawa | |
| 2004/0181148 A1* | 9/2004 | Uchiyama | G01N 21/474 600/425 |
| 2011/0178401 A1 | 7/2011 | Ichihara et al. | |
| 2013/0109950 A1 | 5/2013 | Herzog et al. | |
| 2013/0190591 A1* | 7/2013 | Hirson | A61B 8/4444 600/407 |
| 2013/0279920 A1 | 10/2013 | Herzog | |
| 2013/0289381 A1 | 10/2013 | Oraevsky et al. | |
| 2013/0304405 A1* | 11/2013 | Schmid | A61B 5/721 702/56 |
| 2013/0310694 A1* | 11/2013 | Tsujita | A61B 5/0059 600/459 |
| 2014/0051967 A1* | 2/2014 | Irisawa | A61B 1/07 600/407 |
| 2014/0051971 A1 | 2/2014 | Tokita | |

FOREIGN PATENT DOCUMENTS

| | | | | |
|---|---|---|---|---|
| JP | 2012-231978 A | | 11/2012 | |
| JP | 2012228401 A | * | 11/2012 | ............... A61B 1/07 |
| WO | WO 2012/108171 A1 | | 8/2012 | |
| WO | WO-2012108171 A1 | * | 8/2012 | ........... A61B 8/4416 |
| WO | WO 2013/018313 A1 | | 2/2013 | |

OTHER PUBLICATIONS

Advisory Action dated Apr. 12, 2018 in copending U.S. Appl. No. 14/809,755.
Office Action dated Aug. 8, 2017 in copending U.S. Appl. No. 14/809,755.
Office Action dated Dec. 12, 2018 in copending U.S. Appl. No. 14/809,755.
Office Action dated Jan. 25, 2018 in copending U.S. Appl. No. 14/809,755.
Written Opinion and English translation of the Written Opinion of the International Searching Authority (form PCT/ISA/237), dated Apr. 15, 2014, for International Application No. PCT/JP2014/057256.

* cited by examiner

A-A CROSS-SECTION

B-B CROSS-SECTION

FIG. 13A
FIG. 13B
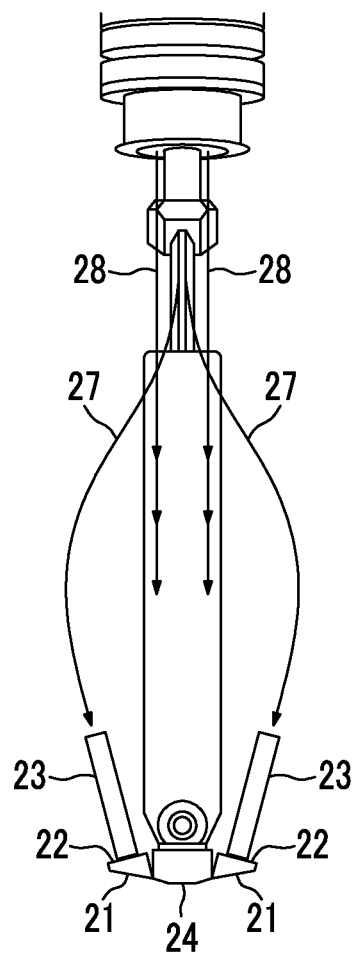
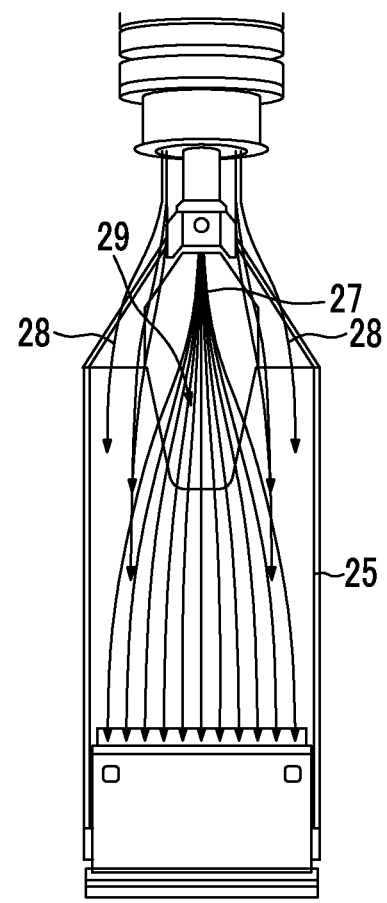

REPLACEMENT METHOD FOR A DAMAGED PART OF A LIGHT EMITTER OF A PROBE

CROSS-REFERENCE TO RELATED APPLICATIONS

This application is a Divisional of copending U.S. patent application Ser. No. 14/809,755, filed Jul. 27, 2015, which is a Continuation of PCT International Application No. PCT/JP2014/057256 filed on Mar. 18, 2014, which claims priority under 35 U.S.C § 119 (a) to Japanese Patent Application No. 2013-063581 filed on Mar. 26, 2013 and Japanese Patent Application No. 2014-050315 filed on Mar. 13, 2014. Each of the above applications is hereby expressly incorporated by reference, in its entirety, into the present application.

BACKGROUND OF THE INVENTION

1. Field of the Invention

The present invention relates to a probe, and more particularly, to a probe that is used for the measurement of photoacoustic waves.

2. Description of the Related Art

An ultrasonic inspection method is known as one kind of image inspecting method that can inspect the internal state of a living body in a non-invasive manner. A probe, which can transmit and receive ultrasonic waves, is used for ultrasonic inspection. When ultrasonic waves are transmitted to a subject (living body) from the probe, the ultrasonic waves travel in the living body and are reflected by a tissue interface. When a distance is calculated on the basis of a time until the reflected ultrasonic waves return to the probe after the reflected ultrasonic waves are received by the probe, an image of the inner state of the living body can be made.

Further, photoacoustic imaging, which makes an image of the inside of a living body by using a photoacoustic effect, is known. In general, the inside of the living body is irradiated with pulsed laser light, such as laser pulses, in photoacoustic imaging. In the living body, biological tissue absorbs the energy of the pulsed laser light and ultrasonic waves (photoacoustic signals) are generated due to adiabatic expansion caused by the energy. When the photoacoustic signals are detected by a probe or the like and a photoacoustic image is formed on the basis of detection signals, the inside of the living body can be made visible on the basis of the photoacoustic signals.

In the photoacoustic imaging, pulsed laser light is guided to the probe from a laser light source and is emitted from a light source provided in the probe. For example, JP2012-231978A discloses a probe including a light emitting unit. In JP2012-231978A, light emitted from a laser light source is guided to the probe through a bundled fiber. A light emitting end of the bundled fiber forms a light emitting unit that emits light to a subject, and is mounted on a housing together with an ultrasonic vibrator.

Further, JP2012-179350A discloses a probe emitting light, which is guided to a probe through an optical fiber or the like, to a subject through a light guide plate that is disposed in the probe. In JP2012-179350A, the light guide plate (light guide member) includes two light guide members. Of the two light guide members, the light guide member positioned on a light incident side is made of glass and the light guide member positioned on a light emitting side is made of a resin. JP2012-179350A also discloses that a light incident surface of the light guide member positioned on the light emitting side serves as a diffusion surface diffusing light.

SUMMARY OF THE INVENTION

Here, the intensity of light to be emitted is relatively high in the photoacoustic imaging. It is considered that the light incident surface of the light guide plate is damaged during the repetition of the emission of light when light is incident on the light guide plate from an optical fiber or the like and is emitted to a subject from the light guide plate. Since the light guide plate (light emitting unit) is generally fixed to the tip of the probe by bonding or the like, the light emitting unit cannot be easily removed from the probe. The light emitting unit is also adapted to be capable of being removed from the probe. However, since the tip of the probe is not sealed in that case, a gap may be formed between a housing and the light emitting unit.

The invention has been made in consideration of the above-mentioned circumstances, and an object of the invention is to provide a photoacoustic probe which prevents the formation of a gap and of which a portion of a light emitting unit to be easily damaged can be replaced.

In order to achieve the above-mentioned object, the invention provides a probe including an acoustic wave detector that detects acoustic waves, a light emitting unit that emits light emitted from a light source toward a subject, and a frame body that holds the acoustic wave detector and the light emitting unit. The light emitting unit includes first and second light guide members that are arranged in series in a traveling direction of light, the first light guide member positioned close to a subject is undetachably fixed to the frame body, and the second light guide member positioned close to the light source is detachably fixed to the frame body.

In the invention, the first light guide member is bonded and fixed to the frame body. In this case, it is preferable that a refractive index of an adhesive, which is used to bond the first light guide member, is lower than a refractive index of the first light guide member.

In the invention, the first light guide member may be formed integrally with the frame body and may be made of transparent rubber. "Transparent" means that light is transmitted without being attenuated much. For example, a member, which transmits 85% or more of incident light, is defined as a transparent member.

The light emitting unit may include a light diffusion layer between the first and second light guide members.

A lens diffusion plate can be used as the light diffusion layer. In this case, it is preferable that an adhesive containing a white pigment is used to fix the lens diffusion plate to the frame body.

In the invention, it is preferable that the light diffusion layer and the first light guide member face each other with a gap therebetween.

It is preferable that a width of a light incident surface of the first light guide member is greater than a width of a light emitting surface of the second light guide member.

Side surfaces of the first light guide member except for the light incident surface and a light emitting surface may be surrounded by the frame body.

The acoustic wave detector may include at least a plurality of detector elements that are arranged one-dimensionally, and the light emitting unit may be positioned on at least one side of the acoustic wave detector in a direction orthogonal to an arrangement direction of the plurality of detector elements so as to be adjacent to the acoustic wave detector.

An optical wire, which guides light emitted from the light source to a light incident surface of the second light guide member, may include a bundled fiber including a plurality of optical fibers, and light emitting ends of the plurality of optical fibers may be arranged in the same direction as the arrangement direction of the plurality of detector elements.

The probe of the invention may further include a fiber guide that is detachably mounted on the second light guide member and allows the light emitting ends of the optical fibers to be arranged along the light incident surface of the second light guide member.

In the probe of the invention, the second light guide member is easily replaced even when the second light guide member is damaged during the repetition of the emission of light. Meanwhile, a gap between the frame body and the first light guide member can be blocked.

BRIEF DESCRIPTION OF THE DRAWINGS

FIG. 13A is a view showing the contents of the probe from the side and FIG. 13B is a view showing the contents of the probe from the front side.

DESCRIPTION OF THE PREFERRED EMBODIMENTS

Figure 1:
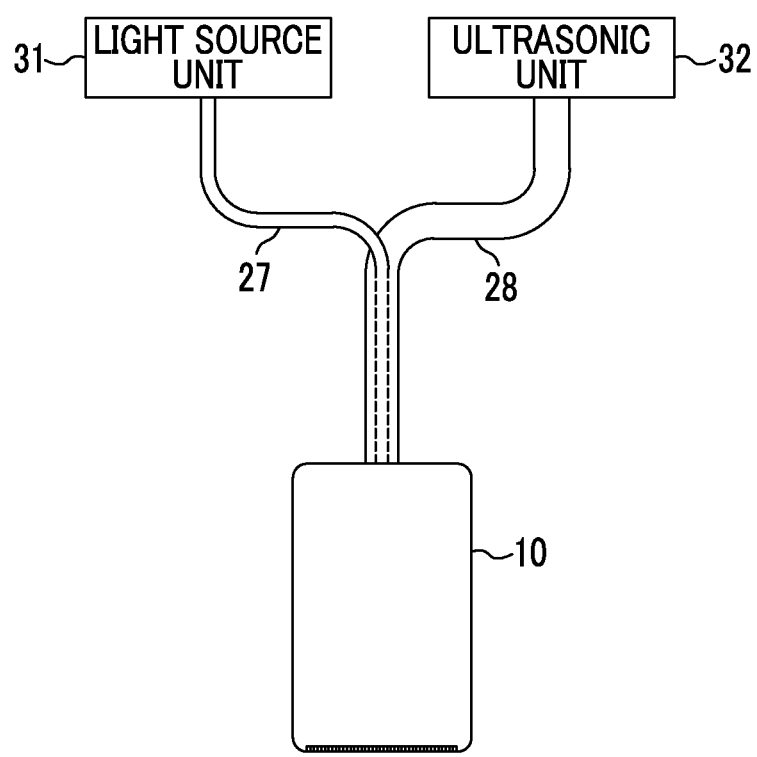
FIG. 1 is a block diagram showing a photoacoustic measurement device including a probe according to an embodiment of the invention.

An embodiment of the invention will be described in detail below with reference to the drawings. FIG. 1 shows a photoacoustic measurement device (photoacoustic image generating device) including a probe according to an embodiment of the invention. The photoacoustic image generating device includes a probe 10, a light source unit 31, and an ultrasonic unit 32. The light source unit 31 is, for example, a laser unit that generates pulsed laser light. The ultrasonic unit 32 is a signal processing unit that processes signals detected by the probe 10.

The probe 10 includes light emitting units that emit light to a subject, and an acoustic wave detector that can detect at least acoustic waves from the subject. The probe 10 is connected to the light source unit 31 through optical wires 27 such as optical fibers. The optical wires 27 include, for example, a plurality of optical fibers. Light emitted from the light source unit 31 is guided to the probe 10 through the optical wires 27, and is emitted to the subject from the light emitting units of the probe 10. The probe 10 detects photoacoustic waves that are generated in the subject due to the application of light after light is emitted to the subject.

The probe 10 is connected to the ultrasonic unit 32 through electrical wires 28. Detection signals (photoacoustic signals) of the photoacoustic waves, which are detected by the probe 10, are transmitted to the ultrasonic unit 32 through the electrical wires 28 and are processed by the ultrasonic unit 32. The ultrasonic unit 32 generates a photoacoustic image on the basis of the photoacoustic signals. The generation of the photoacoustic image includes the reconstruction of the photoacoustic signals, detection, logarithmic transformation, and the like. Meanwhile, the generation of an image is not essential, and certain signal processing merely may be performed on the photoacoustic signals in the ultrasonic unit 32.

Figure 2:
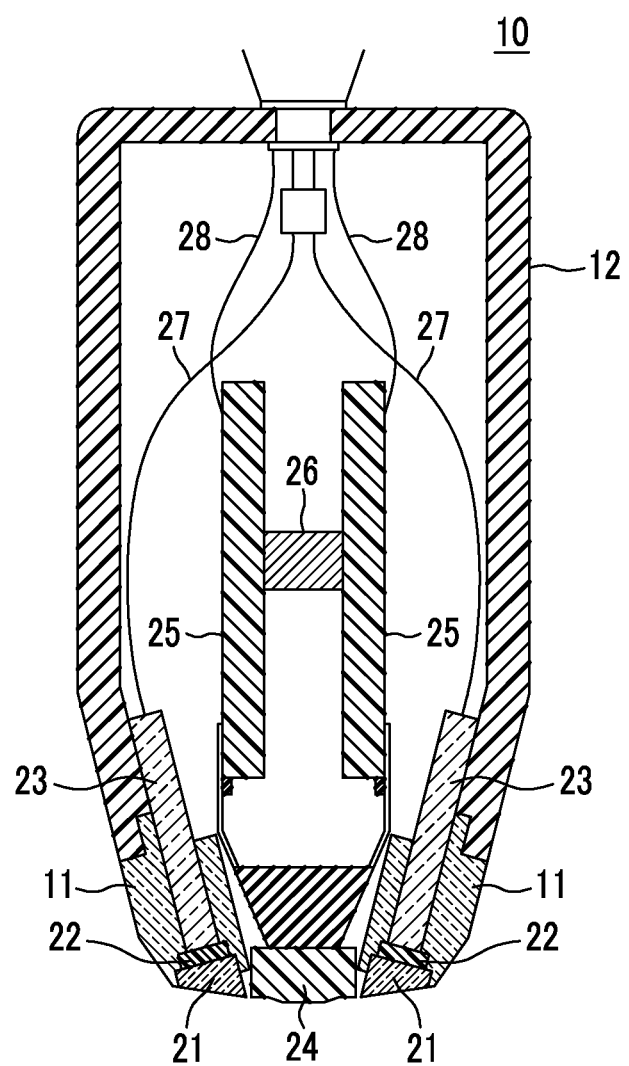
FIG. 2 is a sectional view showing the lateral section of the probe.

FIG. 2 shows the lateral section of the probe. The probe 10 includes first light guide members 21, diffusion plates 22, second light guide members 23, an acoustic wave detector 24, and substrates 25. The first light guide members 21, the diffusion plates 22, and the second light guide members 23 form the light emitting units that emit light emitted from a light source toward the subject. The first light guide members 21, the diffusion plates 22, and the second light guide members 23, which form the light emitting units, and the acoustic wave detector 24 are held by a frame body 11 that forms a tip portion of the probe 10. Meanwhile, the diffusion plates 22 may be omitted.

The first and second light guide members 21 and 23 are arranged in series in the traveling direction of light. Light emitting ends of the optical wires 27 are optically connected to light incident ends of the second light guide members 23. The second light guide members 23 guide light, which is emitted from the light source and incident from the optical wires 27, toward the subject. Light emitted from the second light guide members 23 is diffused by the diffusion plates 22 corresponding to a light diffusion layer, and is then incident on light incident surfaces of the first light guide members 21. Since the diffusion plate 22 is provided between the first and second light guide members 21 and 23, illumination unevenness can be reduced. The width of the light incident surface of the first light guide member 21 is greater than the width of a light emitting surface of the second light guide members 23. The width of the light incident surface or the light emitting surface of the light guide member is defined by the length of both or one of sides of, for example, a rectangular light incident surface or a rectangular light emitting surface. The first light guide members 21 emit diffused light to the subject from light emitting surfaces thereof.

The acoustic wave detector 24 detects acoustic waves generated from the subject. The acoustic wave detector 24 includes, for example, a plurality of ultrasonic vibrators (detector elements) that are arranged at least one-dimensionally. The substrates 25 are connected to the acoustic wave detector 24, and the electrical wires 28 are connected to the substrates 25. For example, amplifiers, which amplify photoacoustic signals detected by the acoustic wave detector 24, and the like are mounted on the substrates 25. The photoacoustic signals detected by the acoustic wave detector 24 are amplified by the amplifiers mounted on the substrates 25, and are then transmitted to the ultrasonic unit 32 (see FIG. 1) through the electrical wires 28. The acoustic wave detector 24 and the substrates 25 are mounted on a frame 26.

In FIG. 2, the light emitting units, which include the first light guide members 21, the diffusion plates 22, and the second light guide members 23, are provided on both sides of the acoustic wave detector 24 in a direction orthogonal to the arrangement direction of the ultrasonic vibrators so as to be adjacent to the acoustic wave detector 24. However, the light emitting units do not need to be provided on both sides, and may be provided on one side. Since the light emitting surfaces of the first light guide members 21 are positioned next to the acoustic wave detecting surface of the acoustic wave detector 24, light can be emitted to the subject from the positions close to the acoustic wave detector 24. Further, the light emitting units are inclined with respect to the acoustic wave detecting surface of the acoustic wave detector 24 at, for example, an angle larger than 0° and not larger than 45° so that light emitted from the light emitting units is directed to the center of the rectangular acoustic wave detector in a lateral direction. Accordingly, light can be emitted to a position directly below the acoustic wave detector 24.

Figure 3:
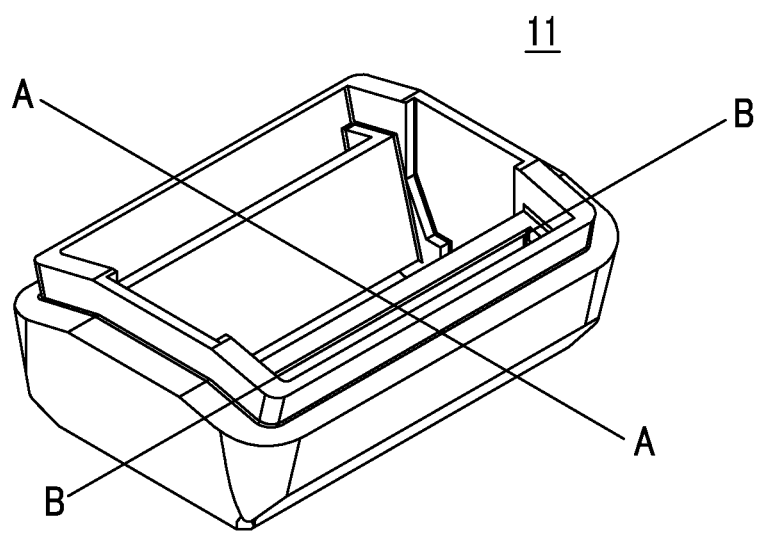
FIG. 3 is a perspective view of a frame body.
Figure 4:
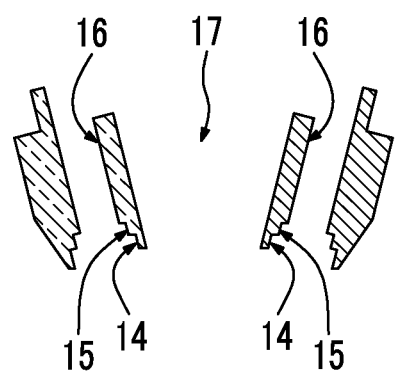
FIG. 4 is a cross-sectional view taken along A-A of FIG. 3.
Figure 5:
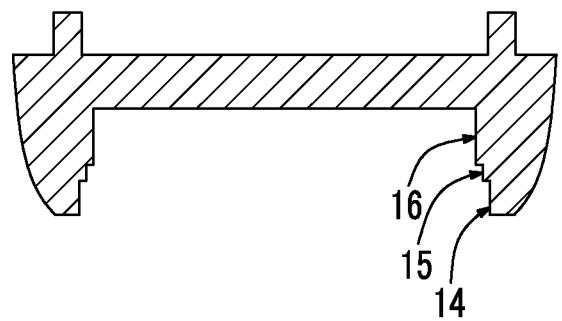
FIG. 5 is a sectional view taken along B-B of FIG. 3.

FIG. 3 is a perspective view of the frame body 11 that is seen from the side of the frame body on which the second light guide members 23 are mounted. FIG. 4 shows a cross-section taken along A-A of FIG. 3, and FIG. 5 shows a section taken along B-B of FIG. 3. As shown in FIGS. 4 and 5, the frame body 11 includes housing portions 14 in which the first light guide members 21 are mounted, housing portions 15 in which the diffusion plates 22 are mounted, and housing portions 16 in which the second light guide members 23 are mounted. Furthermore, as shown in FIG. 4, the frame body 11 includes a housing portion 17 which is formed at a middle portion of the frame body and in which the acoustic wave detector 24 is mounted. The width of the housing portion 14 in which the first light guide member 21 is mounted is greater than the width of the housing portion 15 in which the diffusion plate 22 is mounted. Moreover, the width of the housing portion 15 in which the diffusion plate 22 is mounted is greater than the width of the housing portion 16 in which the second light guide member 23 is mounted.

Figure 6:
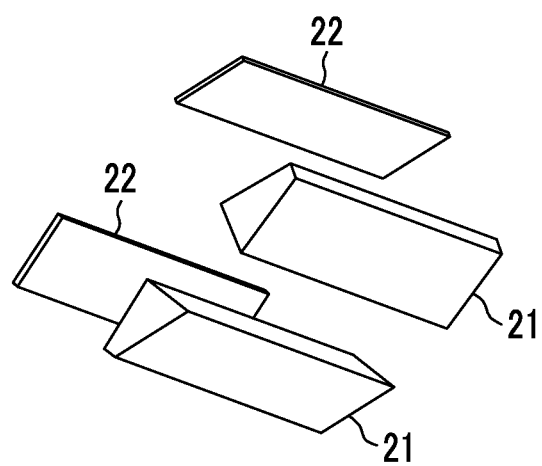
FIG. 6 is a perspective view of first light guide members and diffusion plates.

FIG. 6 is a perspective view of the first light guide members 21 and the diffusion plates 22. The diffusion plates 22 are mounted in the housing portions 15 (see FIGS. 4 and 5) of the frame body 11 when the probe 10 is assembled. The diffusion plates 22 are fixed to the frame body 11 by, for example, an adhesive or the like. After the diffusion plates 22 are mounted, the first light guide members 21 are mounted in the housing portions 14. The first light guide members 21 are fixed to the frame body 11 by, for example, an adhesive or the like. An adhesive of which the refractive index is lower than the refractive index of the first light guide member 21 may be used as the adhesive that is used to fix the first light guide members 21. For example, an epoxy adhesive EPO-TEK 302-FL or EPO-TEK 301 manufactured by Epoxy Technology, Inc. or liquid rubber KE-44-T manufactured by Shin-Etsu Chemical Co., Ltd. can be used as the adhesive. In order to suppress the protrusion (wraparound) of an adhesive to the light incident surface or the light emitting surface of the light guide member, it is preferable that the light guide members are mounted in the frame body 11 after an adhesive is applied to the side surfaces of the light guide members.

Figure 7:
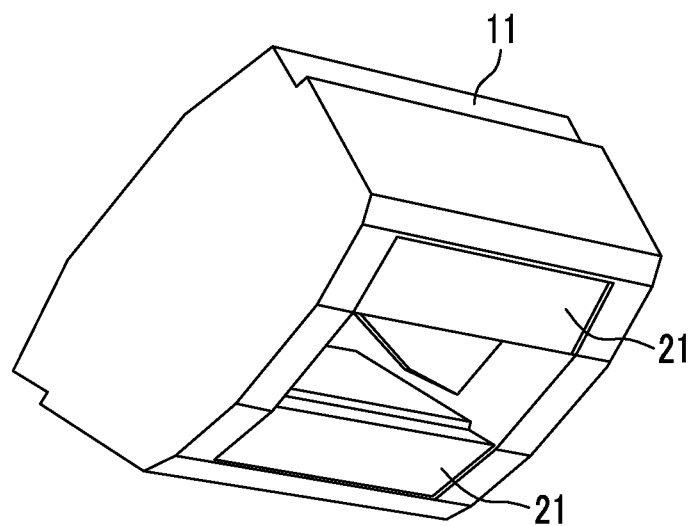
FIG. 7 is a perspective view of a frame body on which the first light guide members are mounted.

FIG. 7 shows the frame body 11 on which the first light guide members 21 are mounted. The diffusion plates 22 are fixed to the back of the first light guide members 21 when seen from the subject. The first light guide members 21 are undetachably fixed to the frame body 11 by an adhesive or the like. The first light guide members 21 are preferably positioned so that the four surfaces of the first light guide member except for the light incident surface facing the diffusion plate 22 and the light emitting surface of the first light guide member facing the subject are surrounded by the frame body 11, and are bonded and fixed. Since the first light guide members 21 are undetachably fixed to the frame body 11, it is possible to prevent the formation of a gap and the like.

Figure 8:
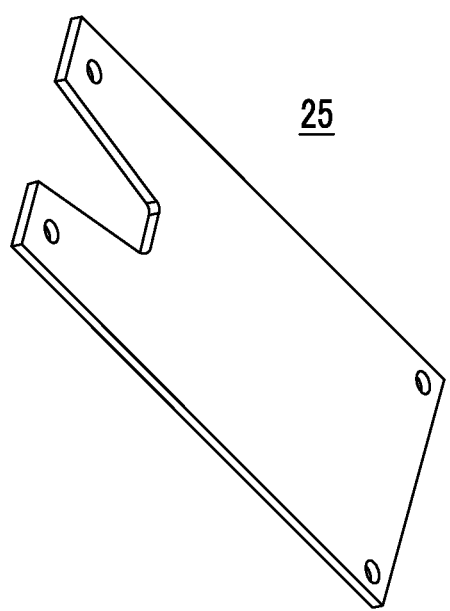
FIG. 8 is a perspective view of a substrate.
Figure 9:
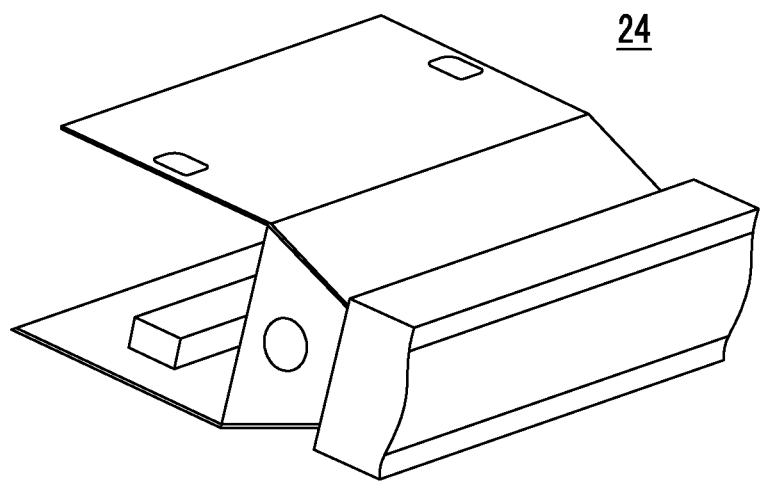
FIG. 9 is a perspective view of an acoustic wave detector.
Figure 10:
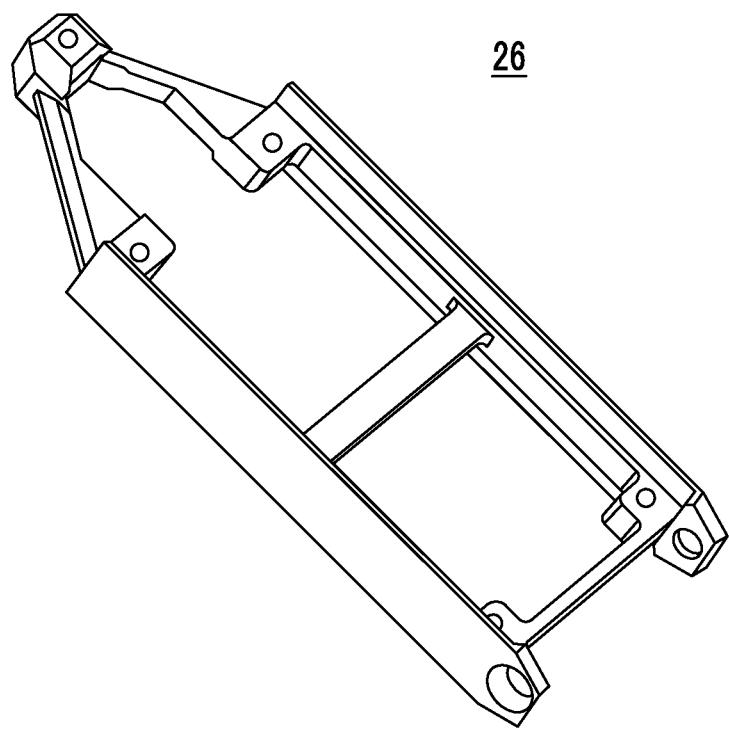
FIG. 10 is a perspective view of a frame.

FIG. 8 shows the substrate 25. An amplifier, which amplifies photoacoustic signals, and the like are mounted on the substrate 25. In addition, an AD converter (Analog-to-digital converter) may be mounted on the substrate 25. FIG. 9 shows the acoustic wave detector 24. The acoustic wave detector 24 includes, for example, the plurality of ultrasonic vibrators (acoustic wave detector elements) that are arranged one-dimensionally in a longitudinal direction. FIG. 10 shows the frame 26. The substrates 25 shown in FIG. 8 are mounted on the surface and back of the frame 26. Further, the acoustic wave detector 24 shown in FIG. 9 is mounted on one end portion of the frame 26. After the acoustic wave detector 24 is mounted on the frame 26, the acoustic wave detector 24 is fixed to the frame 26 and the housing portion 17 (see FIG. 4) of the frame body.

Figure 11:
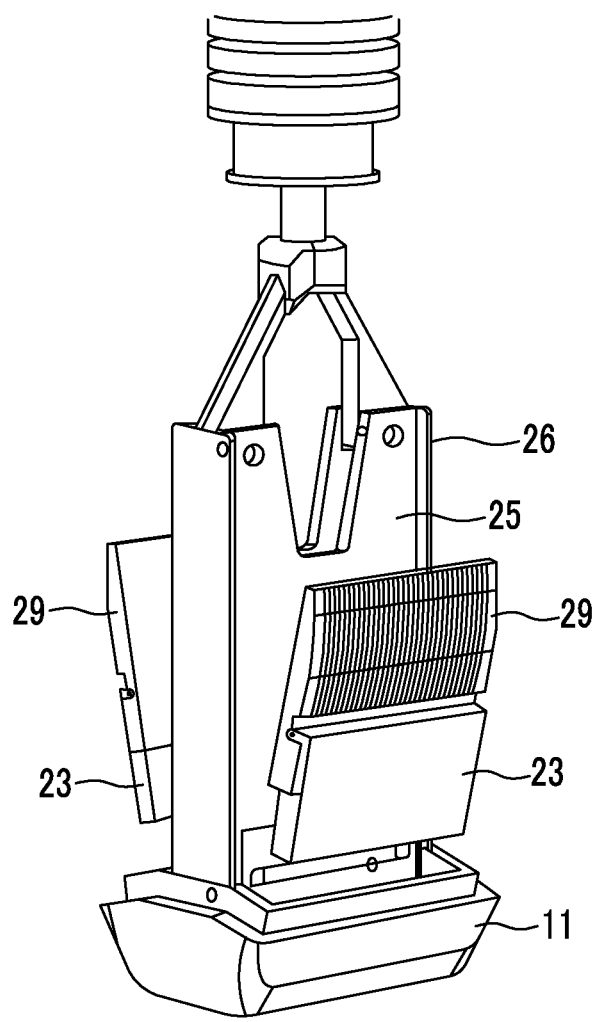
FIG. 11 is a perspective view showing a state in which the frame is mounted on the frame body.

FIG. 11 shows a state in which the frame 26 is mounted on the frame body 11. In FIG. 11, fiber guides 29 are mounted on the second light guide members 23. For example, element wires of a bundled fiber used as the optical wire 27 (see FIG. 1) are arranged on the fiber guide 29 in the longitudinal direction of the light incident surface of the second light guide member 23. The respective element wires of the bundled fiber are positioned relative to the light incident surface of the second light guide member 23 by the fiber guide 29. The second light guide member 23 is pressed from both side surfaces of the fiber guide 29 in the longitudinal direction, so that the fiber guide 29 is mounted on the second light guide member 23. Accordingly, the fiber guide 29 is detachably mounted on the second light guide member 23.

The second light guide members 23 are inserted into the housing portions 16 (see FIGS. 4 and 5) of the frame body 11 and are fixed to the housing portions 16. An adhesive or the like is not used to fix the second light guide members 23, and the second light guide members 23 are detachably fixed to the frame body 11. For example, the second light guide members 23 are fitted and fixed to the frame body 11. The side surfaces of the second light guide members 23 come into surface contact with the side surfaces of the housing portions 16 of the frame body 11, so that the second light guide members 23 are fixed to the frame body 11. Alternatively, some protrusions may be formed on the side surfaces of the housing portions 16 of the frame body 11 and may come into contact with the second light guide members 23, so that the second light guide members 23 are fixed to the frame body 11.

Figure 12:
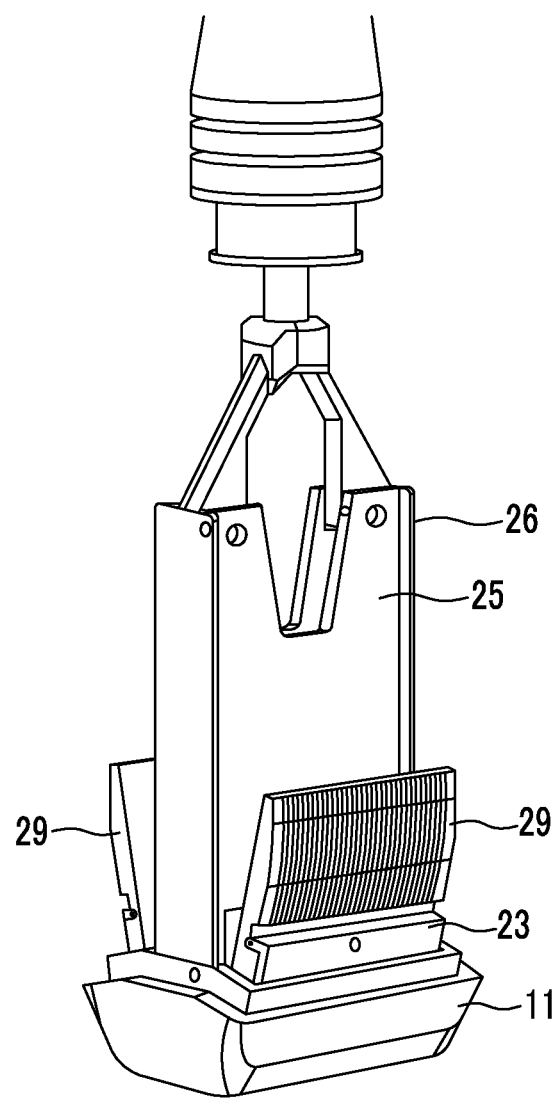
FIG. 12 is a perspective view showing a state in which second light guide members are fixed.

FIG. 12 shows a state in which the second light guide members 23 are fixed. Since the second light guide members 23 are not bonded to the frame body 11 and detachably mounted on the frame body 11, it is easy to replace the second light guide members 23. Meanwhile, since the first light guide members 21 are present on the sides of the second light guide members 23 facing the subject and the first light guide members 21 are undetachably fixed to the frame body 11 by adhesion or the like, it is possible to prevent the formation of a gap and the like. After the second light guide members 23 are fixed, an exterior cover 12 (see FIG. 2) is mounted.

FIG. 13A is a view showing the contents of the probe 10 from the side and FIG. 13B is a view showing the contents of the probe 10 from the front side. Meanwhile, the frame body 11 and the fiber guides 29 are not shown in FIGS. 13A and 13B. A composite cable for electricity and light, which includes the optical wires 27 and the electrical wires 28 (see FIG. 1), is connected to the probe 10. The optical wires 27 are disposed at the central portion of the composite cable, and the electrical wires 28 are disposed outside the optical wires 27.

For example, a bundled fiber is used as the optical wire 27, and light emitting ends of the respective optical fibers of the bundled fiber are arranged on the light incident surface of the second light guide member 23 in the same direction as the arrangement direction of the ultrasonic vibrators. The same direction as the arrangement direction of the ultrasonic vibrators is in the range of, for example, ±20° with respect to the arrangement direction. A notch 29 is formed at the central portion of the side of the substrate 25 opposite to the acoustic wave detector 24. Since the notch 29 is formed at the substrate 25, interference between the substrate 25 and the optical wires 27 can be prevented when the optical wires 27 are pulled to the light incident end of the second light guide member 23 from the central portion of the composite cable. The electrical wires 28 are mainly connected to both sides of the notch 29 of the substrate 25.

At the time of the replacement of the second light guide members 23, the exterior cover 12 (see FIG. 2) is removed first so that the contents of the probe 10 are seen. Then, the optical wires 27 are removed from the light incident surfaces of the second light guide members 23. After that, the second light guide members 23 are pulled out of the frame body 11 and new second light guide members 23 are inserted and fixed to the frame body 11. Further, after the light emitting ends of the optical wires 27 are mounted on the light incident surfaces of the second light guide members 23, the exterior cover 12 is mounted.

In this embodiment, the light emitting unit includes the first and second light guide members 21 and 23 that are arranged in series in the traveling direction of light. The first light guide member 21, which is the light emitting side, is undetachably fixed to the frame body 11 but the second light guide member 23 is detachably fixed to the frame body 11. Since the first light guide member 21 coming into contact with the subject is, for example, bonded and fixed to the frame body 11, the formation of a gap between the first light guide member 21 and the frame body 11 can be prevented. Meanwhile, since the second light guide member 23, which is positioned closer to the light source than the first light guide members 21, is, for example, fitted and fixed so as to be capable of being removed from the frame body 11, it is possible to easily replace the second light guide member 23 when the end face of the second light guide member 23 on which light is incident from the optical wire 27 is damaged.

An example in which the diffusion plate 22 is used as a light diffusion layer provided between the first and second light guide members 21 and 23 has been described in the above-mentioned embodiment, but the light diffusion layer does not necessarily need to be formed separately from the first and second light guide members 21 and 23. For example, a light diffusion layer or a light diffusion surface may be formed on the light emitting side of the second light guide member 23 so that diffused light is incident on the first light guide member 21. Specifically, unevenness, which diffuses light, may be formed on the light emitting end face of the second light guide member 23 so that the light emitting end face of the second light guide member 23 serves as a light diffusion surface. Alternatively, a light diffusion layer may be formed on the first light guide members 21 so that diffused light is emitted to the subject.

Further, an example in which the first light guide members 21 are mainly bonded and fixed to the frame body 11 has been described in the above-mentioned embodiment, but the invention is not limited thereto. For example, when the frame body 11 is formed by injection molding, the first light guide members 21 may be disposed in a mold and the mold may be filled with a resin or the like so that the formation of the frame body 11 and the fixing of the first light guide members 21 to the frame body 11 are simultaneously performed. Alternatively, a transparent adhesive resin, such as transparent rubber or an epoxy resin, is molded in the frame body 11 after the formation of the frame body 11 so that the transparent adhesive resin forms the first light guide members 21.

Figure 14:
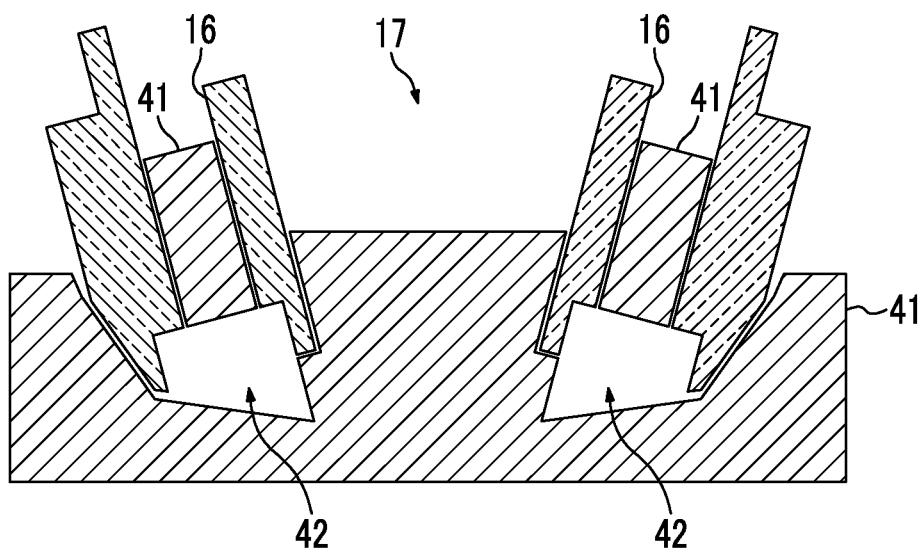
FIG. 14 is a sectional view of the frame body and a mold when molding is performed using a transparent adhesive resin.

FIG. 14 is a sectional view of the frame body 11 and a mold when molding is performed using a transparent adhesive resin. The diffusion plate provided between the first and second light guide members is omitted in this example. When the first light guide members 21 are formed, the frame body 11 is disposed in a mold 41 for molding. The mold 41 is, for example, a metal mold that includes several pieces. The housing portions 16 of the frame body 11 in which the second light guide members 23 are mounted and the housing portion 17 thereof in which the acoustic wave detector 24 (see FIG. 2) are blocked by the mold 41.

Cavities 42 corresponding to the shape of the first light guide member 22 are formed between the frame body 11 and the mold 41. When a transparent adhesive resin is poured into the cavities 42 formed by the mold 41 and is hardened, the transparent adhesive resin is integrated with the frame body 11. The hardened transparent adhesive resin forms the first light guide members 21. For example, transparent rubber, such as KE-109 or KE-106 manufactured by Shin-Etsu Chemical Co., Ltd., is used as the transparent adhesive resin.

The first light guide members 21 and the frame body 11 may be continuously formed. For example, the mold is filled with a resin and the injection molding of the frame body 11 is performed. Then, the frame body 11 is not taken out of the mold and a part of the mold is removed so that the cavities 42 are formed between the mold and the frame body 11. After that, a transparent adhesive resin is poured into the cavities 42 and is hardened, so that the first light guide members 21 integrated with the frame body 11 are formed.

Figure 15:
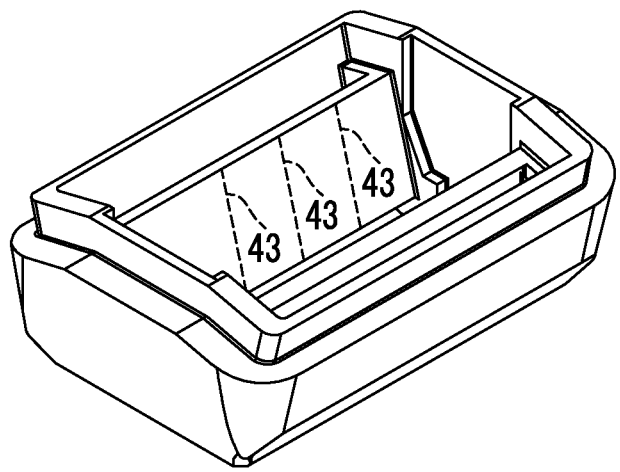
FIG. 15 is a perspective view of the frame body.
Figure 17:
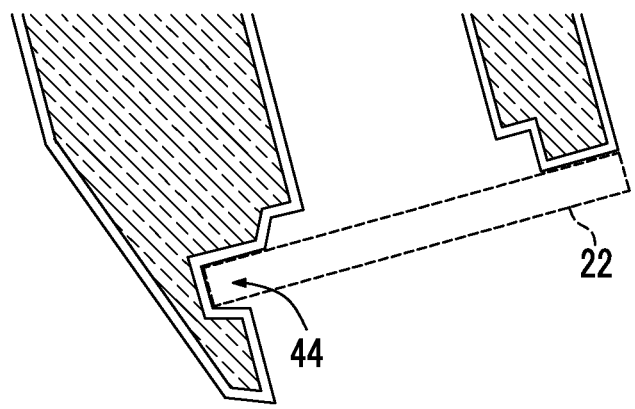
FIG. 17 is a sectional view of a tip portion of the frame body.

FIG. 15 is a perspective view of the frame body 11. The frame body 11 includes grooves 43 formed on the wall facing the housing portion 17. When the cavities 42 formed between the frame body 11 and the mold 41 are filled with a transparent adhesive resin and the transparent adhesive resin is hardened, defective molding occurs if the transparent adhesive resin does not spread into the cavities 42. When the frame body 11 includes the grooves 43 as shown in FIG. 17, air present in the cavities 42 or a part of the transparent adhesive resin can be discharged to the outside of the mold 41 through the grooves 43 during the filling of the cavities with the transparent adhesive resin. Accordingly, the cavities can be smoothly filled with a transparent adhesive resin and the occurrence of defective molding or the formation of a gap between the first light guide member 21 and the frame body 11 can be suppressed.

Figure 16:
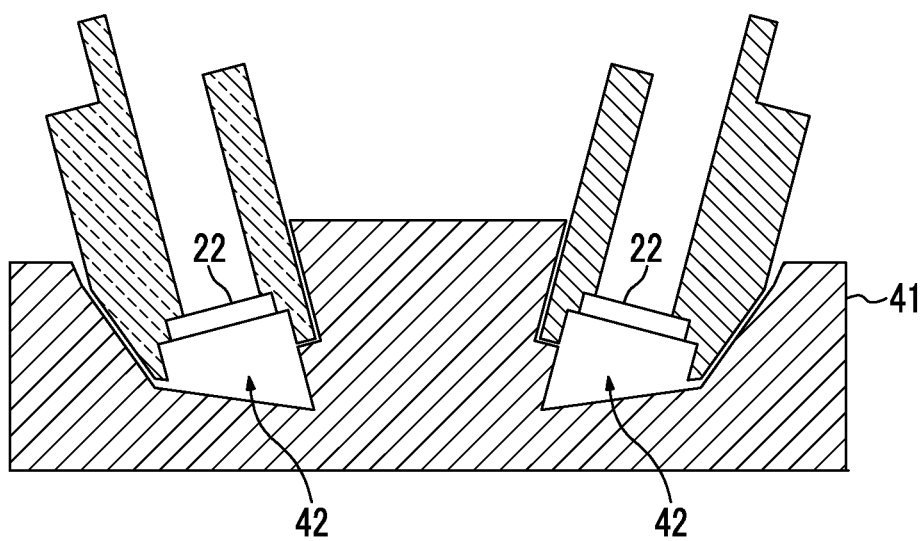
FIG. 16 is a sectional view of another example of the frame body and the mold when molding is performed using a transparent adhesive resin.

FIG. 16 shows the section of another example of the frame body 11 and the mold when molding is performed using a transparent adhesive resin. In this example, diffusion plates 22 are mounted on a frame body 11 by, for example, a transparent adhesive or the like before first light guide members 21 are molded. After the diffusion plates 22 are mounted on the frame body 11, the frame body 11 is disposed in a mold 41. A transparent adhesive resin is poured into the cavities 42 formed between the frame body 11 and the mold 41 and is hardened, so that the diffusion plates 22 and the first light guide members 21 can be integrated with the frame body 11. An ultraviolet curing resin, for example, a low refractive index ultraviolet curing resin OP-3801 manufactured by DIC Corporation can be used as a transparent adhesive that is used for the mounting of the diffusion plates 22. When the transparent adhesive resin is irradiated with ultraviolet rays so as to be hardened, the diffusion plates 22 and the surface of the frame body 11 are treated, so that adhesion between the transparent adhesive resin and the diffusion plates 22 and the surface of the frame body 11 is improved.

For easy mounting of the diffusion plates 22 on the frame body 11, grooves into which the diffusion plates 22 are inserted may be formed on the frame body 11. FIG. 17 shows the section of a tip portion of the frame body 11. The tip portion of the frame body 11 includes a groove 44 that is formed on one side of a position at which the diffusion plate 22 is mounted. When the diffusion plate 22 is mounted, one end portion of the diffusion plate 22 is inserted into the groove 44 after the groove 44 is filled with an adhesive. The other face of the tip portion of the frame body 11 is formed of a flat surface, and the other end portion of the diffusion plates 22 is bonded to the flat surface after an adhesive is applied to the flat surface. Accordingly, the diffusion plates 22 are easily mounted.

A lens diffusion plate can be used as the diffusion plate 22. The lens diffusion plate includes, for example, a plurality of minute lenses that are randomly disposed on the surface thereof, and diffuses light by the minute lenses that are randomly disposed. The lens diffusion plate may diffuse and form light in a circular shape, and may diffuse and form light in an oval shape. It is preferable that a diffusion angle of the lens diffusion plate forming light in a circular shape is in the range of 20° to 80°. It is preferable that a diffusion angle of the lens diffusion plate forming light in an oval shape is 75°×45°, 90°×25°, 90°×60°, and the like. An LSD standard, which is made of polycarbonate or polyester manufactured by Luminit, LLC, can be used as the lens diffusion plate.

It is preferable that an adhesive having high light diffusivity is used to fix the lens diffusion plate to the frame body 11. The reason for this is that intense light may be partially emitted since the light diffusivity of the portion to which the adhesive is applied is lost when an adhesive is applied to a lens diffusion surface. When an adhesive having light diffusivity is used, light can be diffused due to the light diffusivity of the adhesive even though the adhesive is applied to the lens diffusion surface of the lens diffusion plate. An adhesive containing a white pigment, such as silicone rubber to which a white pigment is mixed, can be used as the adhesive. Examples of the white pigment include $TiO_2$. It is preferable that $TiO_2$ content is in the range of 1 wt % to 20 wt %. Specifically, liquid rubber KE-45-W manufactured by Shin-Etsu Chemical Co., Ltd. can be used as the adhesive.

Examples in which a gap is not formed between the diffusion plate 22 and the second light guide member 23 have been shown in FIGS. 2 and 13A, but the invention is not limited thereto. The diffusion plate 22 and the second light guide member 23 may face each other with a gap therebetween. For example, since the fiber guide 29 mounted on the second light guide member 23 bumps against the frame body 11, the movement of the second light guide member 23 toward the diffusion plate 22 is suppressed. Accordingly, a gap may be formed between the diffusion plate 22 and the second light guide member 23.

The invention has been described above on the basis of the preferred embodiment thereof. However, the probe of the invention is not limited to only the above-mentioned embodiment, and various alterations and modifications formed from the structure of the above-mentioned embodiment are also included in the scope of the invention.

EXPLANATION OF REFERENCES

10: probe
11: frame body
12: exterior cover
14 to 17: housing portion
21: first light guide member
22: diffusion plate
23: second light guide member
24: acoustic wave detector
25: substrate
26: frame
27: optical wire
28: electrical wire
29: notch
31: light source unit
32: ultrasonic unit

What is claimed is:
1. A replacement method for a damaged part of a probe, wherein the probe comprises:
an acoustic wave detector that detects acoustic waves;
a light emitter that emits light emitted from a light source toward a subject; and
a frame body that holds the acoustic wave detector and the light emitter,
wherein the light emitter includes a first light guide member and a second light guide plate that are arranged in series in a traveling direction of the light and a light incident surface of the second light guide plate is optically connected to light emitting ends of optical wires which guide the light from the light source to the light incident surface of the second light guide plate,
the first light guide member positioned on the subject side is undetachably fixed to the frame body, and
the second light guide plate positioned on the light source side is detachably fixed to the frame body,
wherein the light emitter has a light diffusion layer between the first light guide member and the second light guide plate,
the light diffusion layer and a light incident surface of the first light guide member are faced at each other with a gap therebetween, and
a width of a light incident surface of the first light guide member is greater than a width of a light emitting surface of the second light guide plate, and
wherein the replacement method comprises:
removing the optical wires from the second light guide plate, pulling out the second light guide plate which is damaged from the frame body, inserting a new second light guide plate to the frame body, and mounting the removed optical wires on the new second light guide plate.

2. The replacement method for a damaged part of the probe according to claim 1, wherein the first light guide member is bonded and fixed to the frame body.

3. The replacement method for a damaged part of the probe according to claim 2, wherein a refractive index of an adhesive, which is used to bond the first light guide member, is lower than a refractive index of the first light guide member.

4. The replacement method for a damaged part of the probe according to claim 1, wherein the first light guide member is formed integrally with the frame body and is made of transparent rubber.

5. The replacement method for a damaged part of the probe according to claim 1, wherein the light diffusion layer is a lens diffusion plate.

6. The replacement method for a damaged part of the probe according to claim 5, wherein the lens diffusion plate is bonded and fixed to the frame body by an adhesive containing a white pigment.

7. The replacement method for a damaged part of the probe according to claim 1, wherein side surfaces of the first light guide member except for a light incident surface and a light emitting surface are surrounded by the frame body.

8. The replacement method for a damaged part of the probe according to claim 1, wherein the acoustic wave detector includes a plurality of detector elements that are arranged at least one-dimensionally, and the light emitter is positioned on at least one side of the acoustic wave detector in a direction orthogonal to an arrangement direction of the plurality of detector elements so as to be adjacent to the acoustic wave detector.

9. The replacement method for a damaged part of the probe according to claim 8, wherein the optical wires include a bundled fiber including a plurality of optical fibers, and light emitting ends of the plurality of optical fibers are arranged in the same direction as the arrangement direction of the plurality of detector elements.

10. The replacement method for a damaged part of the probe according to claim 9, further comprising a fiber guide that is detachably mounted on the second light guide plate and allows the light emitting ends of the optical fibers to be arranged along the light incident surface of the second light guide plate.

* * * * *